(12) United States Patent
Krafczyk et al.

(10) Patent No.: US 6,506,922 B2
(45) Date of Patent: *Jan. 14, 2003

(54) PROCESS FOR THE PRODUCTION OF YELLOW BIS(3-[TRIETHOXYSILYL]-PROPYL) POLYSULFANE

(75) Inventors: Roland Krafczyk, Rheinfelden (DE); Ulrich Deschler, Sailauf (DE); Rudolf Michel, Freigericht (DE); Christoph Batz-Sohn, Hanau-Mittelbuchen (DE)

(73) Assignee: Degussa AG, Dusseldorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/948,712

(22) Filed: Sep. 10, 2001

(65) Prior Publication Data

US 2002/0038043 A1 Mar. 28, 2002

(30) Foreign Application Priority Data

Sep. 13, 2000 (DE) .......................... 100 45 269

(51) Int. Cl.⁷ .................................................. C07F 7/08
(52) U.S. Cl. ....................................................... 556/427
(58) Field of Search .......................................... 556/427

(56) References Cited

U.S. PATENT DOCUMENTS

| 5,489,701 A | * | 2/1996 | Childress et al. | ............ 556/427 |
| 5,596,116 A | * | 1/1997 | Childress et al. | ............ 556/427 |
| 6,380,413 B2 | * | 4/2002 | Krafczyk et al. | ............ 556/427 |

* cited by examiner

Primary Examiner—Margaret G. Moore
(74) Attorney, Agent, or Firm—Pillsbury Winthrop LLP

(57) ABSTRACT

Process for the production of yellow bis(3-[triethoxysilyl] propyl)polysulfane with an average sulfur chain length of less than 4 and an iodine colour value of $\leq 10$ mg iodine/100 ml, wherein neutral chloropropyltriethoxysilane is mixed with chloropropyltrichlorosilane and then reacted with sodium sulfide ($Na_2S$) and sulfur, disodium tetrasulfide ($Na_2S_4$) and $Na_2S$ or disodium trisulfide ($Na_2S_3$) and $Na_2S$ in ethanol.

5 Claims, No Drawings

PROCESS FOR THE PRODUCTION OF YELLOW BIS(3-[TRIETHOXYSILYL]-PROPYL) POLYSULFANE

The invention relates to the production of yellow bis(3-[triethoxysilyl]propyl)polysulfane.

Bis(3-[triethoxysilyl]propyl)disulfane can be produced by the reaction of chloropropyltriethoxysilane with sodium sulfide ($Na_2S$) and sulfur. The chloropropyltriethoxysilane used can be produced by ethanolysis of chloropropyltrichlorosilane. As is known from DE 20 61 189 and DE 32 36 628, a completely reacted product with only a very small proportion of chloropropylmonochlorodiethoxysilane is obtained therefrom. This completely reacted chloropropyltriethoxysilane is referred to below as "neutral".

If the neutral chloropropyltriethoxysilane is reacted with sodium sulfide ($Na_2S$) and sulfur to form bis(3-[triethoxysilyl]propyl)disulfane, a dark-yellow to red coloured product (iodine colour value $\geq 20$ mg iodine/100 ml) is obtained. However, a light-yellow product, which cannot be obtained from neutral chloropropyltriethoxysilane, has been introduced on to the market. In order to obtain light-yellow bis(3-[triethoxysilyl]propyl)disulfane (iodine colour value $\leq 10$ mg iodine/100 ml), a so-called residual acid content must be present in the chlororopyltriethoxysilane in the form of chloropropylmonochlorodiethoxysilane. This can be achieved in that the ethanolysis reaction is not fully completed. However, in operating practice, this measure results in not inconsiderable additional outlay, particularly since the residual acid content has to be kept within a very narrow range and therefore the reaction has to be terminated very specifically at a certain point shortly before complete conversion.

Acidification of the neutral chloropropyltriethoxysilane with alcoholic hydrochloric acid before the reaction with the above-mentioned thionating agents also leads not to light-yellow coloured bis(3-[triethoxysilyl]propyl) disulfane but again to a dark-yellow to red coloured compound.

From EP 0963 995 a process is known for the production of short-chain polysulfide silanes from $M_2S$ or NS with M=alkali metal, ammonium and N =alkaline earth metal, zinc, sulfur and halopropyltrialkoxysilane.

Furthermore, from DE 100 34 493.3 a process is known for the production of organosilyl alkyl polysulfanes by reduction of the sulfur chain length with $M_2S$ and organosilyl alkyl halide. The organosilyl alkyl polysulfane with the original long sulfur chain can also be reacted with the $M_2S$ and the organosilyl alkyl halide as soon as it is formed from organosilyl alkyl halide and $M_2Sy$.

The disadvantage of these known processes lies in the fact that a product with a dark-yellow to red colour is obtained.

From DE 10024037.2 a process for the production of light-yellow bis(3-[triethoxysilyl]propyl)tetrasulfane is known, wherein chloropropyltrichlorosilane is added to neutral chloropropyltriethoxysilane and then reacted with sodium polysulfide or $Na_2S$ and sulfur in ethanol.

The object of the invention is to provide an alternative process with the aid of which a yellow bis(3-[triethoxysilyl]propyl)polysulfane is obtained.

The invention provides a process for the production of yellow bis(3-[triethoxysilyl]propyl)polysulfane with an average sulfur chain length of less than 4, preferably less than 3.1, particularly preferably less than 2.5, and an iodine colour value of $\leq 10$ mg iodine/100 ml, preferably 5–7 mg iodine/100 ml, which is characterised in that neutral chloropropyltriethoxysilane is mixed with chloropropyltrichlorosilane and then reacted with sodium sulfide ($Na_2S$) and sulfur, disodium tetrasulfide ($Na_2S_4$) and $Na_2S$ or disodium trisulfide ($Na_2S_3$) and $Na_2S$ in ethanol. The disodium trisulfide ($Na_2S_3$) can be a 1:1 mixture of $Na_2S_2$ and $Na_2S_4$.

The bis(3-[triethoxysilyl]propyl)polysulfane can be a polysulfane mixture.

In a preferred embodiment, the bis(3-[triethoxysilyl]propylsulfane can be a bis(3-[triethoxysilyl]propyl) disulfane or bis(3-[triethoxysilyl]propyl) trisulfane.

This process has the advantage that the ethanolysis reaction does not have to be specifically terminated at a certain point shortly before complete conversion, but can be carried out to complete conversion to neutral chloropropyltriethoxysilane. The small quantity of chloropropylmonochlorodiethoxysilane required for the production of light-yellow bis(3-[triethoxysilyl]propyl)polysulfane can be achieved simply by adding chloropropyltrichlorosilane to neutral chloropropyltriethoxysilane.

Chloropropyltrichlorosilane can be added to a solution of neutral chloropropyltriethoxysilane and ethanol or chloropropyltrichlorosilane can be added to neutral chloropropyltriethoxysilane and ethanol then added.

Chloropropyltrichlorosilane can be added in quantities of 0.1–20 wt. %, preferably 0.5–5 wt. %, particularly preferably 0.8–1.2 wt. %. The ratio of chloropropyltriethoxysilane: $Na_2S$: S or sodium polysulfide determines the sulfur chain length in bis(3-[triethoxysilyl]propyl)polysulfane.

The reaction mixture can be heated before adding sodium polysulfide and $Na_2S$ or $Na_2S$ and sulfur, preferably to temperatures of 20–90° C.

Bis (3- [triethoxysilyl]propyl) polysulfane produced by the process according to the invention has an iodine colour value of $\leq 10$ mg iodine/100 ml.

EXAMPLES

Example 1

At room temperature, 4.8 g chloropropyltrichlorosilane are added dropwise to a solution of 481.6 g chloropropyltriethoxysilane (neutral) in 480 ml ethanol. The reaction mixture is then boiled for 1 h at 82° C., stirring, with reflux. After cooling to 60° C., 33.7 g sulfur and 89.7 g sodium sulfide ($Na_2S$) are added and the reaction mixture boiled for 1.5 h at 82° C., stirring, with reflux. After cooling to room temperature, the precipitated sodium chloride is removed by filtration and the ethanol removed using a rotary evaporator. A subsequent filtration yields 441.8 g light-yellow bis (3-[triethoxysilyl]propyl)disulfane with an iodine colour value of 5–7 mg iodine/100 ml, the identity of which is confirmed by means of $^1$H-NMR spectroscopy.

Example 2

At room temperature, 2.4 g chloropropyltrichlorosilane are added dropwise to 240.8 g chloropropyltriethoxysilane (neutral). Stirring is then carried out for 1 h at 80° C. After adding 240 ml ethanol, the temperature falls to 60° C., 18.4 g sulfur and 44.8 g sodium sulfide ($Na_2S$) are added and the reaction mixture is boiled for 1.5 h at 81° C., stirring, with reflux. After cooling to room temperature, the precipitated sodium chloride is removed by filtration and the ethanol removed using a rotary evaporator. A subsequent filtration yields 210.4 g light-yellow bis(3-[triethoxysilyl]propyl) disulfane with an iodine colour value of 7–10 mg iodine/100 ml, the identity of which is confirmed by means of $^1$H-NMR spectroscopy.

Example 3

At room temperature, 1.8 g chloropropyltrichlorosilane are added dropwise to a solution of 180.6 g chloropropyltriethoxysilane (neutral) in 180 ml ethanol. The reaction mixture is then boiled for 30 min. at 82° C., stirring, with reflux. After cooling to 60° C., 21.8 g disodium tetrasulfide ($Na_2S_4$) and 19.5 g sodium sulfide ($Na_2S$) are added and the reaction mixture boiled for 2 h at 82° C., stirring, with reflux. After cooling to room temperature, the precipitated sodium chloride is removed by filtration and the ethanol removed using a rotary evaporator. A subsequent filtration yields 163.2 g light-yellow bis(3-[triethoxysilyl]propyl)disulfane with an iodine colour value of 5–7 mg iodine/100 ml, the identity of which is confirmed by means of $^1$H-NMR spectroscopy.

Example 4

At room temperature, 1.2 g chloropropyltrichlorosilane are added dropwise to a solution of 126.4 g chloropropyltriethoxysilane (neutral) in 120 ml ethanol. The reaction mixture is then boiled for 30 min. at 82° C., stirring, with reflux. After cooling to 60° C., 17.8 g disodium trisulfide ($Na_2S_3$) and 10.7 g sodium sulfide ($Na_2S$) are added and the reaction mixture boiled for 2 h at 82° C., stirring, with reflux. After cooling to room temperature, the precipitated sodium chloride is removed by filtration and the ethanol removed using a rotary evaporator. A subsequent filtration yields 122.0 g light-yellow bis(3-[triethoxysilyl]propyl)disulfane with an iodine colour value of 5–7 mg iodine/100 ml, the identity of which is confirmed by means of $^1$H-NMR spectroscopy.

Example 5

Comparative Example 1

At room temperature, 33.7 g sulfur and 89.7 g sodium sulfide ($Na_2S$) are added to a solution of 481.6 g chloropropyltriethoxysilane (neutral) in 480 ml ethanol. The temperature of the reaction mixture rises to 60° C. The reaction mixture is boiled for 1.5 h at 82° C., stirring, with reflux. After cooling to room temperature, the precipitated sodium chloride is removed by filtration and the ethanol removed using a rotary evaporator. A subsequent filtration yields 440.2 g red bis(3-[triethoxysilyl]propyl)disulfane with an iodine colour value of ≧20 mg iodine/100 ml, the identity of which is confirmed by means of $^1$H-NMR spectroscopy.

Example 6

Comparative Example 2

At room temperature, 21.8 g disodium tetrasulfide ($Na_2S_4$) and 19.5 g sodium sulfide ($Na_2S$) are added to a solution of 180.6 g chloropropyltriethoxysilane (neutral) in 180 ml ethanol and the reaction mixture boiled for 2 h at 82° C., stirring, with reflux. After cooling to room temperature, the precipitated sodium chloride is removed by filtration and the ethanol removed using a rotary evaporator. A subsequent filtration yields 161.5 g red bis(3-[triethoxysilyl]propyl) disulfane with an iodine colour value of ≧20 mg iodine/100 ml, the identity of which is confirmed by means of $^1$H-NMR spectroscopy.

Example 7

Comparative Example 3

At room temperature, 17.8 g disodium trisulfide ($Na_2S_3$) and 10.7 g sodium sulfide ($Na_2S$) are added to a solution of 126.4 g chloropropyltriethoxysilane (neutral) in 120 ml ethanol and the reaction mixture boiled for 2 h at 82° C., stirring, with reflux. After cooling to room temperature the precipitated sodium chloride is removed by filtration and the ethanol removed using a rotary evaporator. A subsequent filtration yields 121.1 g red bis(3-[triethoxysilyl]propyl) disulfane with an iodine colour value of ≧20 mg iodine/100 ml, the identity of which is confirmed by means of $^1$H-NMR spectroscopy.

Example 8

At room temperature, 4.8 g chloropropyltrichlorosilane are added dropwise to a solution of 481.7 g chloropropyltriethoxysilane (neutral) in 480 ml ethanol. The reaction mixture is then boiled for 1 h at 82° C., stirring, with reflux. After cooling to 60° C., 50.5 g sulfur and 89.7 g sodium sulfide ($Na_2S$) are added and the reaction mixture boiled for 1.5 h at 82° C., stirring, with reflux. After cooling to room temperature the precipitated sodium chloride is removed by filtration and the ethanol removed using a rotary evaporator. A subsequent filtration yields 492.4 g light-yellow bis(3-[triethoxysilyl]propyl) polysulfane with an average sulfur chain length of 2.5 and an iodine colour value of 5–7 mg iodine/100 ml, the identity of which is confirmed by means of $^1$H-NMR spectroscopy.

Example 9

At room temperature, 4.8 g chloropropyltrichlorosilane are added to a solution of 481.7 g chloropropyltriethoxysilane (neutral) in 480 ml ethanol. The reaction mixture is then boiled for 1 h at 82° C., stirring, with reflux. After cooling to 60° C., 92.2 g sulfur and 89.7 g sodium sulfide ($Na_2S$) are added and the reaction mixture boiled for 1.5 h at 82° C., stirring, with reflux. After cooling to room temperature the precipitated sodium chloride is removed by filtration and the ethanol removed using a rotary evaporator. A subsequent filtration yields 478.8 g light-yellow bis(3-[triethoxysilyl]propyl)polysulfane with an average sulfur chain length of 3.5 and an iodine colour value of 5–7 mg iodine/100 ml, the identity of which is confirmed by $^1$H-NMR spectroscopy.

Example 10

At room temperature, 2.4 g chloropropyltrichlorosilane are added dropwise to a solution of 240.8 g chloropropyltriethoxysilane (neutral) in 180 ml ethanol. The reaction mixture is then boiled for 0.5 h at 82° C., stirring, with reflux. After cooling to 60° C., 44.0 g disodium polysulfide ($Na_2S_{3.8}$) and 20.5 g sodium sulfide ($Na_2S$) are added and the reaction mixture boiled for 2 h at 82° C., stirring, with reflux. After cooling to room temperature the precipitated sodium chloride is removed by filtration and the ethanol removed using a rotary evaporator. A subsequent filtration yields 232.6 g light-yellow bis(3-[triethoxysilyl]propyl) polysulfane with an average sulfur chain length of 2.3 and an iodine colour value of 5–7 mg iodine/100 ml, the identity of which is confirmed by $^1$H-NMR spectroscopy.

The iodine colour value is determined in accordance with din 6162.

The average sulfur chain length is determined by integration of the various $CH_2$-$S_x$ peaks in the $^1$H-NMR spectrum.

What is claimed is:

1. Process for the production of yellow bis(3-[triethoxysilyl]propyl)polysulfane with an average sulfur chain length of less than 4 and an iodine colour value of ≦10 mg iodine/100 ml, characterised in that neutral chloropropyltriethoxysilane is mixed with chloropropyltrichlorosilane and then reacted with sodium sulfide ($Na_2S$) and sulfur, disodium tetrasulfide ($Na_2S_4$) and $Na_2S$ or disodium trisulfide ($Na_2S_3$) and $Na_2S$ in ethanol.

2. Process according to claim 1, characterised in that chloropropyltrichlorosilane is added in a quantity of 0.1–20 wt. %.

3. Process according to claim 1, characterised in that the reaction mixture is heated to 20° C.–90° C. before the addition of sodium sulfide ($Na_2S$) and sulfur, disodium tetrasulfide ($Na_2S_4$) and $Na_2S$, or disodium trisulfide ($Na_2S_3$) and $Na_2S$.

4. Process according to claim 1, characterised in that bis(3-[triethoxysilyl]propyl)polysulfane is a polysulfane mixture.

5. Process according to claim 1, characterised in that the bis(3-[triethoxysilyl]propyl)polysulfane is a bis(3-[triethoxysilyl]propyl)disulfane or bis(3-[triethoxysilyl]propyl)trisulfane.

* * * * *